United States Patent [19]

James, Jr. et al.

[11] Patent Number: 5,358,966
[45] Date of Patent: Oct. 25, 1994

[54] TURFGRASS INSECTICIDES

[75] Inventors: William N. James, Jr., Hatfield; Harold E. Aller, Norristown, both of Pa.

[73] Assignee: Rohm and Haas Company, Philadelphia, Pa.

[21] Appl. No.: 73,842

[22] Filed: Jun. 8, 1993

[51] Int. Cl.$^5$ .......................... A01N 37/18
[52] U.S. Cl. .................................. 514/615
[58] Field of Search ......................... 514/615

[56] References Cited

U.S. PATENT DOCUMENTS

| | | | |
|---|---|---|---|
| 4,985,461 | 1/1991 | Hsu et al. | 514/615 |
| 5,117,057 | 5/1992 | Hsu et al. | 564/149 |

FOREIGN PATENT DOCUMENTS 228564  7/1987  European Pat. Off. .

OTHER PUBLICATIONS

C. Monthean et al., J. Econ. Ent., vol. 85, pp. 507–513 (1992).

Primary Examiner—Richard L. Raymond
Attorney, Agent, or Firm—Clark R. Carpenter

[57] ABSTRACT

This invention relates to a method of controlling insects in turfgrass, ornamental plants or food crops using an insecticidally effective amount of certain N'- substituted-N,N'-diacylhydrazines having the formula

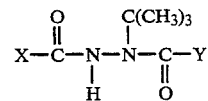

wherein
X is phenyl, 2-fluorophenyl, or phenyl or 2-fluorophenyl substituted at the 4-position with chloro, fluoro, iodo, methyl or ethyl and
Y is phenyl, 4-fluorophenyl, 2-chloro-4-fluorophenyl or phenyl substituted at the 2-position with chloro, bromo or iodo.

11 Claims, No Drawings

TURFGRASS INSECTICIDES

BACKGROUND OF THE INVENTION

This invention relates to a method of controlling insects in turfgrass, ornamental plants or food crops using an insecticidally effective amount of certain N'-substituted-N,N'-diacylhydrazines.

The search for compounds which have a combination of excellent insecticidal activity towards target insects and low toxicity towards non-target species is a continuing one because of factors such as the desire for compounds exhibiting greater activity, better selectivity, lower undesirable environmental impact, lack of phytotoxicity to the locus of application, lower production and market cost and higher effectiveness against insects resistant to many known insecticides. In particular, there exists a need for effective control of Coleopteran larvae (grubs) in turfgrass, ornamental plants and food crops. Commercial insecticides, for example chlorpyrifos, carbaryl, acephate, isofenphos, isazophos, diazinon, ethoprop and bendiocarb, have serious deficiencies such as requiring a high application rate to be effective, possessing undesirable mammalian/arian toxicity, having poor soil mobility, and/or being toxic to beneficial soil animals such as spiders, ants and earthworms.

Although the economic value of the turfgrass industry is difficult to estimate, primarily because much turfgrass acreage is not grown for sale, turfgrass culture in its entirety as an industry contributes significantly to the economy. In the United States, for example, the production, service and maintenance of turfgrass amounts to billions of dollars annually. Protection of existing turfgrass plantings from various pests, including insects, is thus an important concern.

Coleopteran pests are widespread in their habitat. The northern masked chafer, *Cyclocephala borealis* Arrow, and the southern masked chafer, *C. immaculata* (Olivier), are native to the United States and are distributed over a wide area east of the Rocky Mountains. May or June beetles, both Phyllophaga spp. Harris, and the oriental beetle, *Anomala orientalis* Waterhouse, occur throughout Canada and the United States, particularly the eastern half of the United States. The European chafer, *Rhizotrogus (Amphimallon) majalis* (Razoumowsky), is most problematic in the northeastern United States and in Canada. The cupreous chafer, *Anomala cuprea*, is a particular problem for crops and turfgrass in Japan.

In the grub stage, the Japanese beetle, *Popillia japonica* Newman, is undoubtedly the single most important turfgrass-infesting member of the order Coleoptera in the United States. The grub is a major turfgrass pest of golf courses, recreational and industrial parks, school grounds and home lawns. Additionally, it is a major pest as an adult when it feeds on about 300 species of plants, including fruits, vegetables, ornamentals, field and forage crops, and weeds. The beetle's appetite for many ornamental plants greatly increases its pest status in landscape settings. It has a wide geographic distribution in the Northeast and the Midwest of the United States and in Ontario and Quebec in Canada where climatic conditions and large areas of permanent turf favor its development. *Popillia japonica* is is also a pest in Japan where it attacks highland crops and golf course turfgrass.

It is, therefore, an object of the present invention to provide an effective method for controlling insects in turfgrass, ornamental plants or food crops using an insecticidally effective amount of certain N'-substituted-N,N'-diacylhydrazines which have unexpectedly high activity against such pests. Because of this unexpectedly high activity, relatively low application rates of these compounds may be employed while control of the pests is maintained. These relatively low application rates, together with the relatively low mammalian toxicity levels possessed by the compounds of the present invention, result in reduced impact on the environment and reduced risk to the applicator, as well as a lower cost of application. Furthermore, by controlling the larvae or grub in the turfgrass or soil environment, a reduction occurs in the subsequent number of adult insects that feed on foliage, flowers, fruits and vegetables above ground.

U.S. Pat. Nos. 4,985,461 and 5,117,057 describe N'-substituted-N,N'-diacylhydrazines which are useful as insecticides, compositions containing those compounds and methods of their use. However, U.S. Pat. Nos. 4,985,461 and 5,117,057 do not teach or suggest which of these N'-substituted-N,N'-diacylhydrazines are effective for control of insects in turfgrass.

SUMMARY OF THE INVENTION

In accordance with the present invention, there is provided a method of controlling insects which comprises contacting said insects with an insecticidally effective amount of a compound having the formula

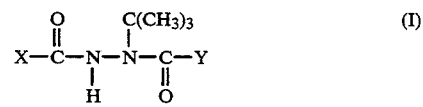

wherein
X is phenyl, 2-fluorophenyl, or phenyl or 2-fluorophenyl substituted at the 4-position with chloro, fluoro, iodo, methyl or ethyl and
Y is phenyl, 4-fluorophenyl, 2-chloro-4-fluorophenyl or phenyl substituted at the 2-position with chloro, bromo or iodo.

Also provided are methods of controlling insects which employ compositions comprising an agronomically acceptable carrier and an insecticidally effective amount of the compounds of the present invention.

DETAILED DESCRIPTION OF THE INVENTION

Compounds employed in the method of the present invention for controlling insects are those of formula (I) wherein X is phenyl, 2-fluorophenyl, or phenyl or 2-fluorophenyl substituted at the 4-position with chloro, fluoro, iodo, methyl or ethyl, and Y is phenyl, 4-fluorophenyl, 2-chloro-4-fluorophenyl or phenyl substituted at the 2-position with chloro, bromo or iodo. Preferred compounds of this group are those compounds wherein X is phenyl, 2-fluorophenyl or 4-chlorophenyl and Y is phenyl, 4-fluorophenyl or phenyl substituted at the 2-position with chloro, bromo or iodo. More preferred compounds are those wherein Y is phenyl, 4-fluorophenyl or 2-chlorophenyl. Most preferred compounds are those wherein Y is phenyl.

Typical compounds utilized in the methods within the scope of the present invention include, but are not limited to:
N'-tert-butyl-N,N'-dibenzoylhydrazine, N'-tert-butyl-N-benzoyl-N'-(4-fluorobenzoyl)hydrazine, N'-tert-butyl-N-benzoyl-N'-(2-chlorobenzoyl)hydrazine, N'-tert-butyl-N-benzoyl-N'-(2-chloro-4-fluorobenzoyl)hydrazine, N'-tert-butyl-N-(4-methylbenzoyl)-N'-benzoylhydrazine, N'-tert-butyl-N-(4-chlorobenzoyl )-N'-benzoylhydrazine, N'-tert-butyl-N-(4-chlorobenzoyl)-N'-(2-chlorobenzoyl)hydrazine, N'-tert-butyl-N-benzoyl-N'-(2-bromobenzoyl)hydrazine, N'-tert-butyl-N-(4-ethylbenzoyl)-N'-benzoylhydrazine, N'-tert-butyl-N-(2-fluorobenzoyl)-N'-benzoylhydrazine, N'-tert-butyl-N-benzoyl-N'-(2-iodobenzoyl)hydrazine, N'-tert-butyl-N-(4-fluorobenzoyl)-N'-benzoylhydrazine, N'-tert-butyl-N-(4-iodobenzoyl)-N'-benzoylhydrazine and N'-tert-butyl-N-(4-fluorobenzoyl)-N'-(2-chlorobenzoyl)hydrazine.

The preferred compounds of these examples include:
N'-tert-butyl-N,N'-dibenzoylhydrazine,
N'-tert-butyl-N-(2-fluorobenzoyl)-N'-benzoylhydrazine and
N'-tert-butyl-N-(4-chlorobenzoyl)-N'-benzoylhydrazine.

The most preferred compound of these examples is N'-tert-butyl-N-(4-chlorobenzoyl-N'-benzoylhydrazine.

General Methods of Preparation

The compounds which are utilized in the method of the present invention, and the intermediates related thereto, can be prepared by methods similar to the known methods for making N'-substituted-N,N'-diacylhydrazines. Such methods are described in U.S. Pat. No. 5,110,986 and in U.S. Pat. No. 5,117,057 ("Process A," "Process B: Method 2," and "Process D").

Representative Compounds Used in the Method of the Present Invention

Table I lists representative compounds used in the method of the present invention. These compounds are provided merely to illustrate their methods of preparation and their use in the method of the present invention. They are not intended to limit the scope of the invention which is defined by the claims.

TABLE I $$X-\underset{H}{\underset{|}{C}}-\underset{}{\overset{O}{\overset{\|}{C}}}-N-N-\underset{\overset{\|}{O}}{\overset{C(CH_3)_3}{\underset{|}{C}}}-Y$$

| COMPOUND | X | Y | MELTING POINT °C. |
|---|---|---|---|
| 1 | PHENYL | PHENYL | 174–176 |
| 2 | 4-CHLOROPHENYL | PHENYL | 197–198 |
| 3 | 2-FLUOROPHENYL | PHENYL | 152–155 |
| 4 | PHENYL | 4-FLUOROPHENYL | 212–213 |
| 5 | 4-CHLOROPHENYL | 2-CHLOROPHENYL | 186–189 |
| 6 | PHENYL | 2-CHLOROPHENYL | 182–184 |
| 7 | PHENYL | 2-BROMOPHENYL | 184–187 |
| 8 | PHENYL | 2-IODOPHENYL | 80–82 |
| 9 | PHENYL | 2-CHLORO-4-FLUOROPHENYL | 164–165 |
| 10 | 4-ETHYLPHENYL | PHENYL | 197–200 |
| 11 | 4-FLUOROPHENYL | PHENYL | 196–198 |
| 12 | 4-IODOPHENYL | PHENYL | 213–216 |
| 13 | 4-FLUOROPHENYL | 2-CHLOROPHENYL | 160.5–163 |
| 14 | 4-METHYLPHENYL | PHENYL | 213–214.5 |

PREPARATION OF COMPOUND 2

N'-tert-Butyl-N-(4-Chlorobenzoyl)-N'-Benzoylhydrazine

Step a. Preparation of N'-tert-Butyl-N-(4-Chlorobenzoyl)hydrazine

To a five liter (L) round bottom flask equipped with a mechanical stirrer, low temperature thermometer and two 500 milliliter (mL) addition funnels is charged 346.8 grams (g) of tert-butylhydrazine hydrochloride, 240 mL of water, 222.6 g of 50% by weight aqueous sodium hydroxide and 2 L of methylene chloride. One addition funnel is charged with 411.6 g of 4-chlorobenzoyl chloride and the second addition funnel is charged with 224 g of 50% by weight sodium hydroxide and 250 mL of water. The reaction flask is placed on an isopropyl alcohol/dry ice cooling bath and a vigorous stirring is started and maintained. When the temperature of the mixture reaches $-15°$ C., a simultaneous and dropwise addition of the 4-chlorobenzoyl chloride and the sodium hydroxide is started with the rate of addition being adjusted in such a way as to keep the temperature in the reaction flask between $-15°$ and $-10°$ C. The addition takes approximately one hour after which time the cooling bath is removed and the reaction mixture is allowed to go to room temperature during a 2-3 hour period. The stirring is then stopped, the phases are allowed to separate and the heavier organic phase is siphoned off using a suction flask. After the lighter aqueous phase is diluted with one liter of water, it is stirred briefly with 500 mL of methylene chloride and the resulting heavier organic phase again is removed using suction. This procedure is repeated with a second 500 mL of methylene chloride. The resulting three separate organic phases are then combined and the solvent is stripped using a rotary evaporator. Hexane, approximately 800 mL, is then added to the residue, the mixture is shaken, and the hexane is removed by filtration on a glass fritted Buchner funnel. The filter cake is washed with about 5 L of water, then about 2 L of hexane, and then is air-dried for a one hour period. After the cake is transferred onto a large dish, it is dried for about 2-3 hours in vacuo, at 65° C. The resulting N'-tert-butyl-N-(4-chlorobenzoyl)-hydrazine intermediate, 571 g, still contains some water, but this is of no consequence to the following step.

Step b. Preparation of N'-tert-Butyl-N-(4-Chlorobenzoyl)-N'-Benzoylhydrazine

To a 5 L round bottom flask, equipped with a mechanical stirrer, containing the 571 g of wet N'-tert-butyl-N-(4-chlorobenzoyl)hydrazine intermediate and equipped with a 500 mL addition funnel containing 371 g of benzoyl chloride, is charged 1500 mL of methylene chloride, 250 mL of water and lastly 223 g of 50% by weight aqueous sodium hydroxide. The flask contents are stirred and cooled to 5° C. and the benzoyl chloride is added dropwise during a one hour period so that the temperature of the flask contents does not exceed 10° C. After allowing the flask contents to warm to room temperature, stirring is stopped and the organic and aqueous phases are allowed to separate overnight. The upper aqueous phase is removed by suction and is replaced by 500 mL of fresh water, the heterogeneous mixture is stirred, the phases are allowed to separate and the upper aqueous phase again is removed by suction. This washing procedure is repeated two more times and then 500–800 mL of hexane is added to the organic remainder. The contents are briefly stirred and then are poured onto a glass flitted Buchner funnel. The filter cake is washed extensively with a total of 2 L of hexane followed by 10 L of water and then is dried in vacuo at 65° C. for two days to give 758.2 g of N'-tert-butyl-N-(4-chlorobenzoyl)-N'-benzoylhydrazine as a white powder melting at 197°–198° C.

Using the appropriate aroyl chloride and the above procedure or a procedure discussed previously in the "General Methods of Preparation" section, compounds 1 and 3–14 of Table I, among others, are also prepared.

Biological Test Method and Data

Test Method

Solutions of the compound to be tested at an application rate of 1.0 pound/acre (lb/a), which is equivalent to approximately 1.121 kilograms/hectare (kg/ha), are prepared by dissolving the appropriate weight of the compound in one milliliter (mL) of acetone and adding nine mL of distilled water containing 0.25% by weight of a surfactant mixture {1/1 ratio of a surfactant composition containing 97–99% by weight of octylphenoxypolyethoxyethanol and 1–3% by weight of polyethylene glycol and a surfactant composition containing 77% by weight of a modified phthalic/glycerol alkyl resin and 23% by weight of butyl alcohol}.

Test soil is prepared by mixing nine parts by volume of air-dried clay loam topsoil with one part by volume of air-dried peat humus. Moisture is added to the soil by incorporating 190 mL of distilled water per 1000 mL of soil. The soil mixture is measured in 100 mL portions into 500 mL glass jars.

A solution, four mL, of the compound to be tested is pipetted into the 100 mL of soil contained in the glass jars. After complete mixing, the test soil and test solution are divided into two 3 ounce metal ointment tins. Ten fertile Japanese beetle (*Popillia japonica*) eggs are placed into a shallow opening in the soil of each tin. The eggs are covered with soil and a small quantity of Red Top grass seed is sprinkled on the surface. The tins are covered with a tight-fitting cap and are held at 80° F. for the three week test period. At 7 and 14 days post-infestation, the soil in each tin is remixed and reseeded. At 21 days post-infestation, the number of live grubs are counted and compared to the controls. Results are reported as percent mortality, corrected for control mortality (Abbott, 1925), for compounds 1–14 employed in the method of this invention (Table II).

TABLE II

BIOLOGICAL DATA ON SOME COMPOUNDS USED IN THE METHOD OF THE PRESENT INVENTION

| COMPOUND | % MORTALITY AT 1.0 LB/A |
|---|---|
| 1 | 100 |
| 2 | 100 |
| 3 | 100 |
| 4 | 87 |
| 5 | 88 |
| 6 | 76 |
| 7 | 76 |
| 8 | 76 |
| 9 | 67 |
| 10 | 69 |
| 11 | 69 |
| 12 | 69 |
| 13 | 65 |
| 14 | 56 |

Uses of the Invention

As previously noted, the compounds used in the method of the present invention exhibit excellent insecticidal activity, particularly upon those insects from the order Coleoptera when these insects are in the larvae or grub stage. More particularly, this excellent insecticidal activity is exhibited upon the southern masked chafer, the northern masked chafer, the European chafer, the cupreous chafer, the oriental beetle, the May beetle and, most particularly, the Japanese beetle.

The compositions and compounds used in the method of this invention can be applied directly to the locus to be protected, for example, the area around or upon economic plants such as turfgrass, ornamental plants or food crops infected with insects or to such economic plants on which infestation is to be prevented or to an area where turfgrass, ornamental plants or foodcrops are to be grown. In particular, the compositions and compounds used in the method of this invention are useful for controlling insects in turfgrass or in an area where turfgrass is to be grown. The compounds and compositions may be used either as contact or systemic pesticides.

In the practice of the method of this invention, the active compound may be applied to the soil or foliage where it is absorbed by the plant or turfgrass, translocated to other plant parts, in particular to the root systems of such plants or turfgrass, and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application.

In general, for the control of insects in turfgrass, ornamental plants and food crops, the compounds utilized in the method of the present invention may be used at a dosage corresponding to from about 100 grams to about 4 kilograms, preferably from about 200 grams to about 3 kilograms, of the active substance per hectare. For the more preferred compounds utilized in the method of the present invention for control of insects, a dosage corresponding to from about 100 grams to about 2 kilograms, preferably from about 250 grams to about 1.5 kilograms, of the active substance per hectare can be employed. The exact amount of dosage for a situation can be routinely determined and depends upon a variety of factors, for example, the substance used, the kind of insect, the formulation used, the state of the crop infested with the insect and the prevailing weather conditions. The term "insecticidal" as employed in the specification and claims of this application is to be construed as any means which adversely affects the existence or growth of the target insects. Such means can comprise a complete killing action, eradication, arresting in growth, inhibition, reducing in number, imparting sterility or any combination thereof. The term "control" as employed in the specification and claims of this application is to be construed as meaning "insecticidal" or protecting plants from insect damage. By "insecticidally effective amount" is meant that dosage of active substance sufficient to exert insect control.

The compounds of the present invention, for practical applications, can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse or diffuse the active ingredient in the composition without impairing the active ingredient's effectiveness and which by itself has no significant detrimental effect on the soil, equipment, desirable plants, or agronomic environment. If desired, conventional adjuvants such as surfactants, stabilizers, antifoam agents and antidrift agents may also be combined.

Examples of compositions and formulations according to this invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. Baits are preparations generally comprising a food or other substance attractive to insects, that includes at least one compound used in the method of the instant invention. The invert emulsions are mainly used for air application, where large areas are treated with a comparatively small amount of preparation and may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional pesticide dispersible liquid diluent carriers and/or dispersible solid carriers optionally with the use of carrier vehicle assistants such as conventional pesticide surface-active agents, including emulsifying agents and/or dispersing agents, whereby, for example, when water is used as diluent, organic solvents may be added as auxiliary solvents. The following may be chiefly considered for use as conventional carrier vehicles for this purpose:

aerosol propellants which are gaseous at normal temperatures and pressures, such as halogenated hydrocarbons as well as propane, butane, nitrogen and carbon dioxide;

inert dispersible liquid diluent carriers including inert organic solvents, such as aromatic hydrocarbons, cycloalkanes, paraffins, chlorinated aliphatic hydrocarbons, vegetable oils, alcohols as well as ethers and esters thereof, amines, amides, sulfoxides, acetonitrile, ketones, and/or water;

solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates;

solid carriers for granules include crushed and fractionated natural rocks such as calcite, marble, pumice, sepiolite and dolomite as well as synthetic granules of organic material such as sawdust, coconut shells, corn cobs and tobacco stalks.

The following may be chiefly considered for use as conventional carrier vehicle assistants:

emulsifying agents, such as cationic and/or non-ionic and/or anionic emulsifying agents; and/or dispersing agents, such as lignin, sulfite waste liquors, methyl cellulose, etc.

Adhesives such as carboxymethylcelluose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments and organic dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is used in an amount substantially between about 0.0001% and 5%, preferably between about 0.001% and 3%, by weight of the mixture. Thus the method of the present invention contemplates the use of formulations and compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, and an amount of the active compound generally between about 0.0001% and about 99% by weight of the composition, preferably between about 0.001% and about 90% by weight of the composition, and more preferably between about 0.01% and about 75% by weight of the mixture which is effective for the purpose in question. The active compounds can be applied as insecticide sprays by methods commonly employed, such as conventional high-gallonage hydraulic sprays, low gallonage sprays, ultra-low-volume sprays, high pressure liquid injection, slit injection, airblast spray, aerial sprays, and dusts.

Furthermore, the present invention contemplates methods of killing, combatting or controlling insects which compromises contacting insects with a correspondingly combative or toxic amount (i.e. an insecticidally effective amount) of at least one active compound of the invention alone or together with a carrier vehicle (composition or formulation) as noted above. The term "contacting" as employed in the specification and claims means applying to at least one of (a) such insects and (b) the corresponding habitat thereof (i.e., the locus to be protected, for example, to a growing crop or to an area where a crop is to be grown) the active compound of this invention alone or as a constituent of a composition or formulation. The formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of insects to be controlled and degree of infestation. Therefore, in special cases, it is possible to go above or below the aforementioned concentration ranges.

In addition to the aforementioned ingredients, the formulations and compositions according to the invention may also contain other substances commonly used in preparations of this kind.

For example, a lubricant, such as calcium stearate or magnesium stearate, may be added to a wettable powder or to a mixture to be granulated. Furthermore there may, for example, be added "adhesives" such as polyvinyl alcohol-cellulose derivatives or other colloidal materials, such as casein, to improve the adherence of the pesticide to the surface to be protected.

Compositions and formulations according to the present invention may also include other known pesticidal compounds. This expands the spectrum of activity of the preparation and may give rise to synergism.

The following known insecticidal, fungicidal and acaricidal compounds are suitable for use in such a combined preparation.

1. Insecticides such as acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, Bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropropylate, chlorphoxim, chlorpyrifos, chlorpyrifos methyl, chlorthiophos, clofentezine, CPCBS, CPMC, crotoxyphos, crufomate, cryolite cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoatemethyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tefluthrin, temephos, TEPP, terbufos, tetrachlorvinphos, tetradifon, tetramethrin, tetrasul, thallium sulfate, thiocarboxime, thiocyclamhydrogenoxalate, thiometon, tolclofos-methyl, toxaphene, triazophos, trichlorfon, trichloronate, triflumuron, trimethacarb, vamidothion, xylylcarb.

2. Fungicides which can be combined with the insecticides used in this invention include:
    (a) dithiocarbamate and derivatives such as ferbam, ziram, maneb, mancozeb, zineb, propineb, metham, thiram, the complex of zineb and polyethylene thiuram disulfide, dazomet, and mixtures of these with copper salts;
    (b) nitrophenol derivatives such as dinocap, binapacryl, and 2-sec-butyl-4,6-dinitrophenyl isopropyl carbonate;
    (c) heterocyclic structures such as captan, folpet, glyodine, anilazine, ditalimfos, 4-butyl-1,2,4- triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozlin, iprodione, procymidone, triadimenol, triadimefon, bitertanol, prochloraz, fenasimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, fenbuconazole, hexaconazole, cyproconazole, terbuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as griseofulvin, kasugamycin, polyoxin, validamycin, and streptomycin;

(f) copper-based fungicides such as copper hydroxide, cuprous oxide, basic cupric chloride, basic copper carbonate, copper terephthalate, copper naphthenate and Bordeaux mixture; and (g) miscellaneous fungicides such as dodine, phenylmercuric acetate, phenylmercuric monoethanol ammonium lactate, N-ethylmercuri-1,2,3,6-tetrahydro-3,6-endomethano-3,4,5,6,7,7-hexachlorophthalimide, p-dimethylaminobenzene sodium sulfonate, methylisothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

It should be understood that the instant specification and examples are set forth by way of illustration and not limitation, and that various modifications and changes may be made without departing from the spirit and scope of the present invention as defined by the appended claims.

We claim

1. A method of controlling the larvae or grub of insects which comprise the southern masked chafer, the northern masked chafer, the Japanese beetle, the European chafer, the cupreous chafer, the oriental beetle and the May or June beetle which comprises contacting the larvae or grub in the soil with an insecticidally effective amount of a compound selected from N'-tert-butyl-N-benzoyl-N'-(4-fluorobenzoyl)hydrazine,
N'-tert-butyl-N-benzoyl-N'-(2-chlorobenzoyl)hydrazine,
N'-tert-butyl-N-benzoyl-N'-(2-chloro-4-fluorobenzoyl)hydrazine,
N'-tert-butyl-N-(4-methylbenzoyl)-N'-benzoylhydrazine,
N'-tert-butyl-N-(4-chlorobenzoyl)-N'-benzoylhydrazine,
N'-tert-butyl-N-(4-chlorobenzoyl)-N'-(2-chlorobenzoyl)hydrazine,
N'-tert-butyl-N-benzoyl-N'-(2-bromobenzoyl)hydrazine,
N'-tert-butyl-N-(4-ethylbenzoyl)-N'-benzoylhydrazine,
N'-tert-butyl-N-(2-fluorobenzoyl)-N'-benzoylhydrazine,
N'-tert-butyl-N-benzoyl-N'-(2-iodobenzoyl)hydrazine,
N'-tert-butyl-N-(4-fluorobenzoyl)-N'-benzoylhydrazine,
N'-tert-butyl-N-(4-iodobenzoyl)-N'-benzoylhydrazine and
N'-tert-butyl-N-(4-fluorobenzoyl)-N'-(2-chlorobenzoyl)hydrazine.

2. The method of claim 1 wherein the compound is selected from
N'-tert-butyl-N-(2-fluorobenzoyl)-N'-benzoylhydrazine,
N'-tert-butyl-N-benzoyl-N'-(4-fluorobenzoyl)hydrazine,
N'-tert-butyl-N-(4-chlorobenzoyl)-N'-(2-chlorobenzoyl)hydrazine and
N'-tert-butyl-N-(4-chlorobenzoyl)-N'-benzoylhydrazine.

3. The method of claim 1 wherein the compound is N'-tert-butyl-N-(4-chlorobenzoyl)-N'-benzoylhydrazine.

4. The method of claim 1 wherein the compound is applied at from about 100 grams to about 4 kilograms per hectare.

5. The method of claim 4 wherein the compound is applied at from about 200 grams to about 3 kilograms per hectare.

6. The method of claim 1 wherein the insect is the Japanese beetle.

7. The method of claim 1 wherein the compound is applied to an area where turfgrass, ornamental plants or food crops are grown or will be grown.

8. The method of claim 7 wherein the compound is applied to turfgrass.

9. The method of claim 1 wherein the compound is applied as a constituent of a composition comprising an insecticidally effective amount of the compound and an agronomically acceptable carrier.

10. The method of claim 9 wherein the compound is present at from about 0.0001 to about 99% by weight of the composition.

11. The method of claim 9 wherein the agronomically acceptable carrier is a solid.

* * * * *